United States Patent
Kobayashi

(10) Patent No.: US 6,280,627 B1
(45) Date of Patent: Aug. 28, 2001

(54) LIQUID CHROMATOGRAPH WITH FRACTION COLLECTOR

(75) Inventor: Masato Kobayashi, Kyoto (JP)

(73) Assignee: Shimadzu Corporation (JP)

( * ) Notice: Subject to any disclaimer, the term of this patent is extended or adjusted under 35 U.S.C. 154(b) by 0 days.

(21) Appl. No.: 09/473,254

(22) Filed: Dec. 27, 1999

(30) Foreign Application Priority Data

Jan. 25, 1999 (JP) .................................................. 11-015626

(51) Int. Cl.[7] .................................................... B01D 15/08
(52) U.S. Cl. ........................ 210/656; 210/659; 73/61.52; 73/61.56
(58) Field of Search .................................. 210/656, 659; 73/61.52, 61.56

(56) References Cited

U.S. PATENT DOCUMENTS 5,135,718 * 8/1992 Kawaguchi et al. .
5,240,577 * 8/1993 Jorgenson et al. .
5,338,514    8/1994 Morabito et al. .
5,462,660 * 10/1995 Singleton et al. .
6,077,438 * 7/2000 Zambias et al. .

FOREIGN PATENT DOCUMENTS 4130028    4/1992 (JP) .
96/ 40398 12/1996 (WO) .

* cited by examiner

Primary Examiner—Duane Smith
Assistant Examiner—Betsey Morrison Hoey
(74) Attorney, Agent, or Firm—Coudert Brothers

(57) ABSTRACT

A fraction collecting device for a liquid chromatograph has a splitter disposed downstream to a chromatographic column and serving to split the flow from the column into two flow routes individually connected to a mass analyzer serving as a detector and a fraction collector. A plurality of pipes each having a different flow resistance and being connected in parallel with respect to one other are inserted in either of these two flow routes. A control unit serves to select one of these pipes according to inputted parameters indicating the conditions of liquid chromatography to be carried out and controls valves so as to connect this selected one of the pipes to the column through the splitter.

2 Claims, 1 Drawing Sheet

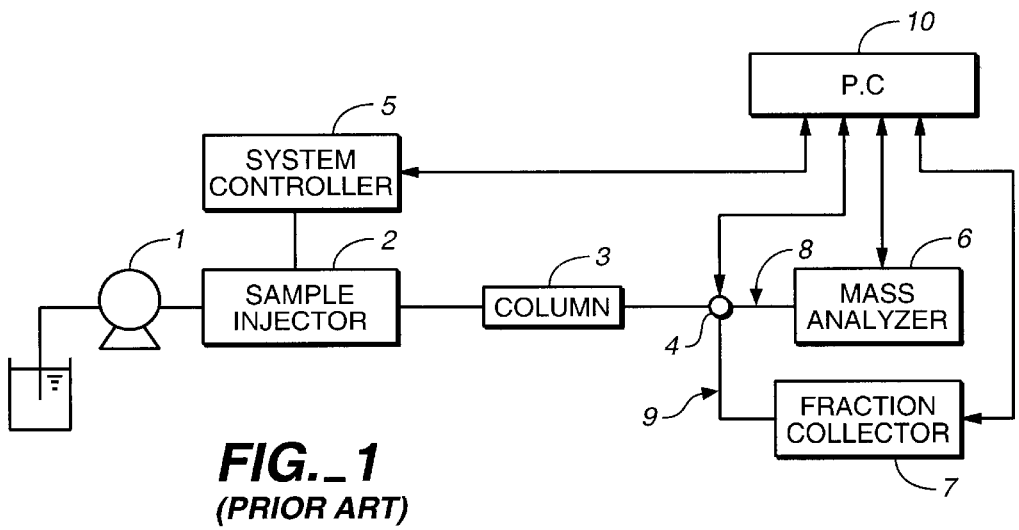
FIG._1
*(PRIOR ART)*
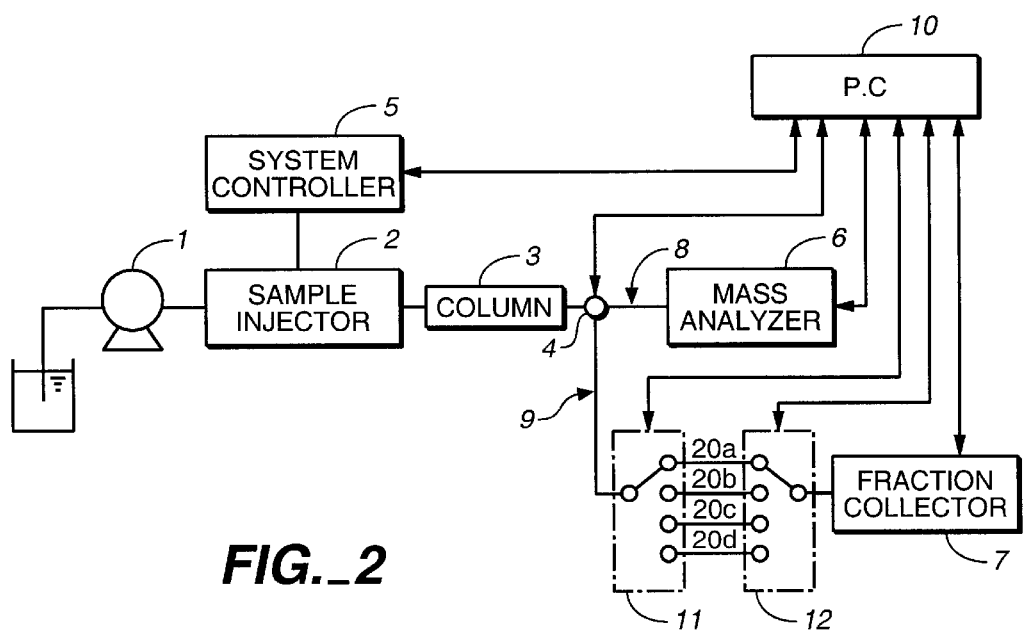
FIG._2

LIQUID CHROMATOGRAPH WITH FRACTION COLLECTOR

BACKGROUND OF THE INVENTION

This invention relates to a liquid chromatograph with a fraction collector and more particularly to such a liquid chromatograph using a mass analyzer as the fraction collector.

As a technology related to liquid chromatography, it has been known to provide a fraction collector on the downstream side of the flow route so as to selectively collect only a target component contained in a sample. Normally, the part of a liquid chromatograph serving to collect a fraction (herein referred to as the "fraction collecting device") includes a liquid pump, a sample injector, a column, a detector, a fraction collector and a system controller for controlling the collection of the fraction. When the detector detects the peak of the target component, the device functions so as to activate a switch valve when the component corresponding to this peak arrives at the switch valve of the fraction collector for its collection. An ultraviolet visible light detector is usually used as the detector for monitoring the sample solution flowing through a flow cell provided on the downstream side of the column.

Recently, a mass analyzer is coming to be used instead of an ultraviolet visible light detector for collecting a fraction with high accuracy. A prior art fraction collecting device for a liquid chromatograph using a mass analyzer as its detector is shown in FIG. 1 wherein numeral 1 indicates a liquid pump, numeral 2 indicates a sample injector, numeral 3 indicates a column for separating components, numeral 4 indicates a splitter, numeral 5 indicates a system controller, numeral 6 indicates a mass analyzer serving as a detector, numeral 7 indicates a fraction collector, numeral 8 indicates a flow route for carrying out the analysis, numeral 9 indicates a fraction collector flow route, and numeral 10 indicates a control unit comprising a personal computer. A fraction collecting device using a mass analyzer as its detector is characterized as being provided with a splitter 4 for branching the flow route into the route for analysis 8 connected to the mass analyzer and the fraction collector flow route 9 connected to the fraction collector. The flow rate of the mobile phase is normally maintained at about several tens of ml/min when the collection of a fraction is carried out, but since the maximum flow rate to the mass analyzer is only 2 ml/min, only a small portion of the sample solution eluted from the column 3 is arranged to be branched into the mass analyzer 6. Since the mass analyzer 6 analyzes a sample solution by ionizing it and its collection becomes difficult after the analysis, only a portion of the sample solution is used for the analysis and the rest is directed for collection.

Thus, a fraction collecting device for a liquid chromatograph is provided with a splitter on the downstream side of the column but the conditions for the collection of fraction such as the flow rate of the mobile phase must be varied, depending on the kind of the sample to be fractioned. In addition, the mode of ionization such as the electro-spray method and the atmospheric chemical ionization method must also be modified. Thus, the split ratio by means of the splitter must also be adjusted such that an optimum condition can be obtained.

It has been known to exchange the fraction collector flow route from the splitter to the fraction collector in order to change the split ratio until a desired split ratio is obtained according to the sample. It is cumbersome, however, to actually exchange the flow route. The manners in which the screws are tightened may even cause deformations of the pipes and a change in the dead volume.

SUMMARY OF THE INVENTION

It is therefore an object of this invention to provide a fraction collector with an improved capability by eliminating such cumbersome processes and reducing the dead volume.

A fraction collecting device for a liquid chromatograph embodying this invention, with which the above and other objects can be accomplished, may be characterized not only as having a splitter for branching the flow from the column into two flow routes individually connected to a mass analyzer and a fraction collector but wherein a plurality of pipes each having a different flow resistance and connected in parallel with respect to one another are inserted into either of these two flow routes and valves are connected such that one of these parallel-connected pipes can be selectively connected to the column through the splitter. A control unit serves to select one of these plurality of pipes and to cause the valves to connect the selected pipe to the column.

BRIEF DESCRIPTION OF THE DRAWINGS

The accompanying drawings, which are incorporated in and form a part of this specification, illustrate an embodiment of the invention and, together with the description, serve to explain the principles of the invention. In the drawings:

FIG. 1 is a block diagram of a prior art fraction collection device for a liquid chromatograph; and FIG. 2 is a block diagram of a fraction collection device for a liquid chromatograph embodying this invention.

DETAILED DESCRIPTION OF THE INVENTION

The invention is described next by way of an example with reference to FIG. 2 in which like components as in FIG. 1 are indicated by the same numerals and are not repetitiously described.

The example shown in FIG. 2 is different from the prior art device described above with reference to FIG. 1 in that there are four pipes 20a, 20b, 20c and 20d with different flow resistances which are connected in parallel with respect to one another and inserted in the fraction collector flow route 9 and that there are also switch valves 11 and 12 which are connected respectively on their upstream and downstream sides and are adapted to be operated by signals from the control unit 10. The control unit 10 also functions to detect peak signals transmitted from the mass analyzer 6 and to control the valves inside the fraction collector 7.

To start the operation, a mobile phase suitable to the sample to be analyzed is prepared, and necessary condition parameters for the analysis such as the flow rate of the mobile phase, the kind of the mobile phase and the ionization mode are inputted through a keyboard (not shown) of the personal computer of the control unit 10. On the basis of the inputted data, the control unit 10 selects one of the pipes 20a–20d considered to be the best suited in order to obtain a required split ratio and switches the switch valves 11 and 12 such that the selected one of the pipes 20a–20d is connected to the fraction collector flow route 9. A simple way to accomplish this is to preliminarily store in a memory (not shown) of the control unit 10 a table showing the pipe to be selected for each set of condition parameters.

Alternatively, a formula relating the pipe diameter, the flow rate and the split ratio may be preliminarily stored in the memory such that the control unit 10 can make a calculation from the inputted data to select one of the pipes 20a–20d as being the best suited to the given condition.

If the sample is sent in with the selected pipe connected to the fraction collector flow route 9, the sample liquid can be branched at a desired split ratio. When the mass analyzer 6 detects a peak of the desired component from the sample flowing through the flow route 8 for analysis, the valves of the fraction collector 7 are switched at an appropriate timing from the time of detection such that the target component can be selectively collected.

Although the invention was described above with reference to only one example, this example is not intended to limit the scope of the invention. Many modifications and variations are possible within the scope of the invention. For example, the parallel connection of the plurality of pipes 20a–20d need not be inserted into the fraction collector flow route 9 but may be inserted into the flow route 8 for the analysis, although not illustrated in a separate drawing. In summary, the present invention makes it unnecessary to exchange pipes whenever the operating conditions of a liquid chromatograph are changed such that changes in dead volume will not take place and fractions can be collected with improved accuracy.

What is claimed is:

1. A fraction collecting device for a liquid chromatograph, comprising:
   a column for chromatographically separating components;
   a mass analyzer;
   a fraction collector;
   a splitter connected downstream to said column to split a flow from said column into two flow routes which are individually connected to said mass analyzer and to said fraction collector;
   a plurality of pipes each having a different flow resistance, said pipes being connected in parallel and inserted into either of said two flow routes;
   switching means for connecting a different one of said plurality of pipes to said column through said splitter; and
   a control unit serving to select one of said plurality of pipes and causing said switching means to connect said selected pipe to said column through said splitter.

2. The fraction collecting device of claim I wherein said control unit preliminarily stores information relating different conditions for effecting liquid chromatography with each of said plurality of pipes.

* * * * *